(12) United States Patent
Boira Bonhora et al.

(10) Patent No.: US 12,214,920 B2
(45) Date of Patent: Feb. 4, 2025

(54) SYSTEM AND METHOD FOR THE STERILE FILLING OF CONTAINERS

(71) Applicant: GRIFOLS WORLDWIDE OPERATIONS LIMITED, Dublin (IE)

(72) Inventors: Jordi Boira Bonhora, Barcelona (ES); Carlos Roura Salietti, Barcelona (ES); David Pages Becerra, Barcelona (ES)

(73) Assignee: GRIFOLS WORLDWIDE OPERATIONS LIMITED, Dublin (IE)

( * ) Notice: Subject to any disclaimer, the term of this patent is extended or adjusted under 35 U.S.C. 154(b) by 0 days.

(21) Appl. No.: 17/924,344

(22) PCT Filed: May 5, 2021

(86) PCT No.: PCT/EP2021/061885
§ 371 (c)(1),
(2) Date: Nov. 9, 2022

(87) PCT Pub. No.: WO2021/228661
PCT Pub. Date: Nov. 18, 2021

(65) Prior Publication Data
US 2023/0182947 A1    Jun. 15, 2023

(30) Foreign Application Priority Data

May 13, 2020 (EP) ..................................... 20382399

(51) Int. Cl.
*B65B 55/06* (2006.01)
*A61L 2/07* (2006.01)
(Continued)

(52) U.S. Cl.
CPC ................ *B65B 55/06* (2013.01); *A61L 2/07* (2013.01); *A61L 2/24* (2013.01); *B65B 3/003* (2013.01);
(Continued)

(58) Field of Classification Search
CPC .......... B65B 3/003; B65B 55/06; B65B 55/24
(Continued)

(56) References Cited

U.S. PATENT DOCUMENTS 5,476,635 A * 12/1995 Stoker ........................ B01J 3/04
422/26
5,522,724 A * 6/1996 Heilmann .................. A23L 3/08
432/163
(Continued)

FOREIGN PATENT DOCUMENTS

DE         26 288 554 A1    1/1978

OTHER PUBLICATIONS

Autoclave—definition, URL https://www.merriam-webster.com/dictionary/autoclave (Year: 2024).*
(Continued)

*Primary Examiner* — Valentin Neacsu
(74) *Attorney, Agent, or Firm* — Knobbe, Martens, Olson & Bear LLP (57) ABSTRACT

A system for the sterile filling of containers for pharmaceutical products, which includes a device for sterilizing containers and a machine for filling sterilized containers, wherein the device for sterilizing containers includes at least one autoclave, and wherein the system includes an automated container-accumulation device and means for automatically transporting the containers sterilized in the autoclave from said autoclave to the container-filling machine via said container-accumulation device.

15 Claims, 9 Drawing Sheets

(51) Int. Cl.
*A61L 2/24* (2006.01)
*B65B 3/00* (2006.01)
*B65B 7/28* (2006.01)

(52) U.S. Cl.
CPC ............. *B65B 7/28* (2013.01); *A61L 2202/17* (2013.01); *A61L 2202/23* (2013.01)

(58) Field of Classification Search
USPC .................................................. 227/140, 120
See application file for complete search history.

(56) References Cited

U.S. PATENT DOCUMENTS

| | | | | |
|---|---|---|---|---|
| 5,562,882 | A * | 10/1996 | Smith ........................ | A61L 2/06 422/26 |
| 6,177,048 | B1 * | 1/2001 | Lagerstedt ................ | A61L 2/07 422/26 |
| 2022/0257823 | A1 * | 8/2022 | Somma ............... | B29B 17/0412 |
| 2023/0182947 | A1 * | 6/2023 | Boira Bonhora ....... | B65B 55/24 53/426 |

OTHER PUBLICATIONS

Clean—definition, URL https://www.merriam-webster.com/dictionary/clean (Year: 2024).*

Is 100% Sterilisation Achievable in an Autoclave? Medical Equipment Services . URL https://www.mesaustralia.com.au/blogs/news/can-autoclaves-achieve-100-percent-sterilisation#:~: text=The%20quick%20answer%20to%20this,to%20100%25%20sterilisation%20as%20possible. (Year: 2024).*

Sterile—definition, URL https://www.merriam-webster.com/dictionary/STERILE (Year: 2024).*

Sterilize—definition, URL https://www.merriam-webster.com/dictionary/STERILIZE (Year: 2024).*

Anonymous: SP PennTech Equipment Manufacturer for Pharmaceutical and Biotech Industries—Delivering Complete Aseptic Vial Handling Solutions For Injectable, (Vials, Syringes. Cartridges). Ophthalmic & Oral Products in Liquid and Powder Form13 Aug. 2019 (Aug. 13, 2019). XP055735633, Retrieved from the Internet: URL:https://sp-penntech.com/delivering-com plete-aseptic-vial-handling-solutions-for- injectable-vials-syringes-cartridges-ophthalmic-and-oral-products-in-liquid-and-powder-form-129 retrieved on Sep. 30, 2020.

Bausch+strobel: Machine type ME 8081 : precise tray-loading of ampoules, cartridges, small bottles and vials, Jan. 1, 2020 (Jan. 1, 2020) XP055736050, Retrieved from the Internet: URL:https://www.bausch-stroebel.com/en/machines/machine-type-me-8081 retrieved on Oct. 2, 2020.

Bausch+strobel: ME series: tray-loading units of the ME series are designed for precise and space efficient tray-loading of stable containers, Jan. 1, 2020 (Jan. 1, 2020), XP055736061, Retrieved from the Internet: URL:https://www.bausch-stroebel.com/en/machines/me-series [retrieved on Oct. 2, 2020].

Bausch+strobel: 11 Pharmaceutical Packaging Machinery for Pharma: Bausch+Strobel Germany, 1' Jan. 2020 (Jan. 1, 2020), XPO55736070, Retrieved from the Internet: URL:https://www.bausch-stroebel.com/en/mac hines?kw !=16 [retrieved on Oct. 2, 2020].

Bausch+strobel: "SPE series :syringe buffer system", Jan. 1, 2020 (Jan. 1, 2020), XP055736067, Retrieved from the Internet: URL:https://www.bausch-stroebel.com/en/machines/spe-series [retrieved on Oct. 2, 2020] the whole document.

AsepticTechnologies: AT-Closed Vial Manufacturing, YouTube, Jun. 17, 2013 (Jun. 17, 2013), p. 1, XP054980948, Retrieved from the Internet: URL:https://www.youtube.com/watch?v=dFqwdE CDR70 [retrieved on Oct. 2, 2020].

Notification of Transmittal of the International Search Report and the Written Opinion of the International Searching Authority issued Jul. 8, 2021; in PCT/EP2021/061885.

* cited by examiner

SYSTEM AND METHOD FOR THE STERILE FILLING OF CONTAINERS

PRIORITY AND CROSS REFERENCE TO RELATED APPLICATIONS

This application is the U.S. National Phase Application under 35 U.S.C. § 371 of International Application No. PCT/EP2021/061885, filed May 5, 2021, designating the U.S. and published as WO 2021/228661A1 on Nov. 18, 2021, which claims the benefit of European Application No. 20382399.2, filed May 13, 2020. Any and all applications for which a foreign or a domestic priority is claimed is/are identified in the Application Data Sheet filed herewith and is/are hereby incorporated by reference in their entireties under 37 C.F.R. § 1.57.

FIELD

The present application relates to a system and a method for the sterile filling of containers.

BACKGROUND

For a drug or product to be properly sterilised, it is important that the containers of these sterile products are also sterilised in order to minimise the risks of contamination by microbes or particles in the products. Accordingly, containers of products that are ultimately subject to sterilisation should be filled in clean zones. These clean zones have a suitable level of cleanliness for sterilising containers. Only the minimum number of people should be present in said zones, particularly during aseptic production.

Systems for the sterile filling of containers are known. In said systems, the containers pass first through a device for cleaning by washing. Next, the containers are sent to a sterilisation device where they are sterilised. The containers are then transported to a filling machine where they are filled aseptically. The sterilisation device in said systems is a depyrogenation oven or tunnel.

A depyrogenation tunnel is a sterilisation device which produces sterilisation by dry heat. The sterilisation and depyrogenation tunnel comprises an endless variable-speed conveyor; variable air modules which include preheating, sterilisation, cooling and stabilisation modules; electrical systems, instrumentation and control, and allows a reduction in pyrogen levels of at least 3 log. The container flow in the depyrogenation tunnel is unidirectional and laminar. One advantage of depyrogenation tunnels is that the container flow is continuous. Owing to the characteristics of this type of oven, the processes should normally be carried out at high temperatures of approximately 250° C. One drawback of depyrogenation tunnels is that the containers must be closed before sterilisation, and the high process temperatures may cause structural damage to the containers.

Another known sterilisation device is the autoclave. In an autoclave, the processes are carried out discontinuously, and sterilisation takes place in cycles, with a specific number of containers at one time, in batches. The main cycle of the autoclave operates at approximately 122° C. for one hour at 1.1 bar, and also has prior heating/cooling cycles and a final cooling cycle.

Autoclaves have a door through which the operator loads the containers and another door through which the operator unloads said containers. Both doors lead into rooms with different ISO classifications. Normally, the operators collect the containers from the cleaning device and place them in carts of different heights or other moveable supports in order to transport the containers into the autoclave. Said containers are sterilised once the operators have loaded the autoclave. After sterilisation, the operators unload the containers-now sterilised-through the other door of the autoclave, and take said containers to a line of the container-filling system. Next, capping is carried out to close the containers. The presence of this human interaction entails a risk of contamination by microbes and by particles from the protective clothing of the people involved in the operation, contaminating the containers in the process of loading and unloading said containers in the autoclave. All staff (including cleaning and maintenance staff) employed in these clean zones must receive special training in the correct manufacture of sterile products and must perform strict personal hygiene and cleanliness controls, as well as wearing high-quality clothing in order to minimise contamination by microbes and by particles from the protective clothing.

Sterilising containers in an autoclave is therefore a discontinuous process, since the autoclaves must be completely closed during sterilisation. This means that the container-filling machine has a discontinuous input flow of containers, which results in idle times when said machine is not working, and times when said machine has a load higher than its nominal operating load, and the filling machine cannot absorb these peak workloads. This is particularly problematic for a machine for filling medical substances, since owing to the properties of said substances, the machine nozzles dry out, and have a negative impact on the substance to be injected into the containers. The use of an autoclave as a sterilisation device in a system for the sterile filling of containers is therefore not optimal.

The autoclave has several advantages over the depyrogenation tunnel, since it is less harsh on the containers, and allows the containers to be open during the process, avoiding the need to close said containers beforehand and, as already stated, it allows batch operation. This discontinuous operation minimises risk should a fault occur in the sterilisation, as only one batch of containers would be affected. The use of an autoclave with automatic transport means and, preferably, an accumulation device allows the drawbacks of discontinuous operation to be circumvented while maintaining all its advantages.

SUMMARY

In some embodiments, a system for the sterile filling of containers for pharmaceutical products includes a device for sterilizing containers and a sterilized-containers filling machine. In some embodiments, the device for sterilizing containers includes a first autoclave, a second autoclave which is parallel to the first autoclave. In some embodiments, the device for sterilizing containers includes a first autoclave, a second autoclave and a third autoclave which are parallel to the first autoclave.

In some embodiment, the system includes an automated container-accumulation device and means for automatically transporting the sterilized containers from the autoclave to the container-filling machine. In some embodiment, the accumulation device includes an accumulation plate, a buffer.

In some embodiment, the system further includes an accumulator for filling the autoclaves, which includes an automatic container-diverting device and control means programmed to direct the containers to a second autoclave when the first autoclave is in operation. In some embodiment, the system includes a buffer at the output of each autoclave. In some embodiment, the system also includes a container-cleaning device and means for automatically transporting the cleaned containers to the at least one autoclave. In some embodiment, the system also includes a device for capping containers after the filling machine. In some embodiment, the containers are vials.

In some embodiment, the device for sterilizing containers includes an automated autoclave-emptying device which is connected to the container-filling machine through the accumulation device.

In some embodiment, a method for the sterile filling of containers for pharmaceutical products includes cleaning the containers, sterilizing the clean containers, filling the sterilized containers in a clean zone.

In some embodiment, sterilizing the clean containers is carried out in at least one autoclave. In some embodiment, the clean containers are directed by automatic transport means from the cleaning to the sterilization and from the sterilization to the filling step. In some embodiment, the containers are directed from sterilization to the filling using an accumulation device that has an accumulation plate. In some embodiment, the containers are directed from sterilization to the filling using an accumulation device that has a buffer.

In some embodiment, the method further includes arranging a second autoclave parallel to a first autoclave so that, while the clean containers are being sterilized in the first autoclave, the second autoclave is being loaded with new clean containers. In some embodiment, the method includes capping the filled containers.

DETAILED DESCRIPTION

One object of the present invention is to disclose a system for the sterile filling of containers that comprises an autoclave as a sterilisation device, but without the drawback of a discontinuous input of containers to the filling machine.

Moreover, another object of the present invention is to automate the entire system in order to minimise human presence and thus the risk of contamination. However, automation of the process is complicated owing to the different natures of the sterilisation process (which is intermittent) and the cleaning and filling processes (which are continuous).

More specifically, the present invention discloses a novel system wherein the containers are sterilised by the combination of an autoclave and automatic transport means. Said configuration allows the container-filling machine to operate with a continuous input of containers. Preferably, this continuous flow of containers is achieved by the use of parallel autoclaves, a container-accumulation device, a system for automatic transport of containers and/or a combination thereof.

More specifically, the present invention discloses a system for the sterile filling of containers for pharmaceutical products, which comprises a device for sterilising containers and a sterilised-containers filling machine, with the special feature that the device for sterilising containers comprises at least a first autoclave, and that the system comprises an automated container-accumulation device and means for automatically transporting the containers sterilised in the autoclave from said autoclave to the container-filling machine via said container-accumulation device. Preferably, the accumulation device comprises an accumulation plate.

More preferably, the accumulation device comprises a buffer.

Alternatively, the system also comprises a second autoclave, said second autoclave being positioned parallel to said first autoclave. Preferably, the system comprises said second autoclave and a third autoclave parallel to said at least one autoclave. More preferably, the system comprises an automated autoclave-emptying device, said autoclave-emptying device and the container-filling machine being connected via the accumulation device. Still more preferably, the system comprises an accumulator for filling the autoclaves, said accumulator comprising an automatic container-diverting device and control means configured to direct the containers to a second autoclave when the first autoclave is in operation.

The system described, which comprises a system of parallel autoclaves and an accumulation device, makes it possible to obtain a continuous input flow of vials to the machine for filling sterilised containers even when the output from the autoclaves is discontinuous. This allows the autoclave process to be separated from the filling process. In this way, if a fault occurs in the autoclave, which without the parallel configuration would result in the metered-feeding process being halted, which in turn would result in a deterioration of the nozzles of the filling machine, the system can continue to operate using the other autoclave, thanks to the parallel configuration.

Parallel working also allows the system for sterile filling of said containers to be carried out more rapidly, more safely and without human intervention, allowing greater reliability when sterilising the containers.

This configuration makes it possible to do away with the idle times during which the autoclave is not operating that would occur in the prior art, said idle times corresponding to the times during which a first set of sterilised containers is being removed from the autoclave and a new set of containers to be sterilised is being fed into said autoclave. Thus, the system according to the present invention allows the speed of the overall container-filling process to be increased. In addition, the present invention also allows the sterilisation system to be automated, avoiding human contact during the container-sterilisation step. This automation allows the risk of contamination by microbes or particles in the products or materials to be minimised.

Preferably, the system comprises a buffer and a second autoclave, the second autoclave being positioned parallel to a first autoclave as described above.

More preferably, the buffer is positioned between the automated emptying device of the first and second autoclaves and the accumulation plate.

Preferably, the system comprises a buffer at an output of each autoclave.

Preferably, the system comprises a container-cleaning device and means for automatically transporting the cleaned containers to the at least one autoclave. More preferably, the filling machine is a metered-feeding device. Still more preferably, the system comprises a device for capping containers after the filling machine.

Preferably, the containers are jars. More preferably, the containers are vials.

The present invention also discloses a method for the sterile filling of containers for pharmaceutical products, which comprises:
  a step of cleaning containers,
  a step of sterilising the clean containers,
  a step of filling the sterilised containers in a clean zone, with the special feature that the step of sterilising the clean containers is carried out in at least one autoclave, and that the clean containers are directed by automatic transport means from the cleaning step to the sterilisation step and from the sterilisation step to the filling step, said containers being directed from the sterilisation step to the filling step via an accumulation device that comprises an accumulation plate. Preferably, the containers are directed from the sterilisation step to the filling step via an accumulation device which comprises a buffer.

More preferably, the method comprises a step of arranging a second autoclave parallel to a first autoclave so that, while the clean containers are being sterilised in the first autoclave, the second autoclave is being loaded with new clean containers. Still more preferably, the method comprises an additional step of capping the filled containers.

Preferably, the containers are jars. More preferably, the containers are vials.

For a better understanding, the accompanying drawings show an explanatory but non-limiting example of an embodiment of the present invention.

Figure 1:
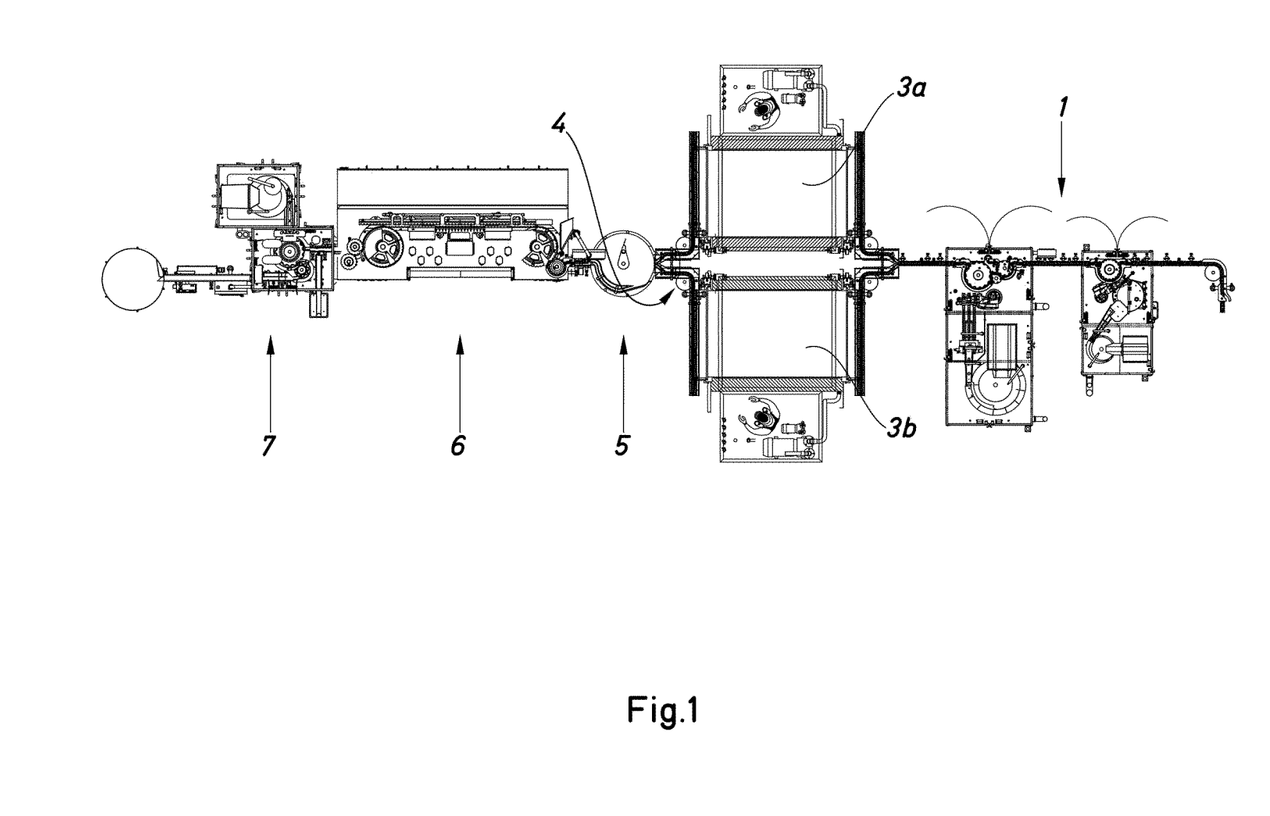
FIG. 1 is a diagram of a first embodiment of a system for the sterile filling of containers for pharmaceutical products, with two parallel autoclaves.
Figure 2:
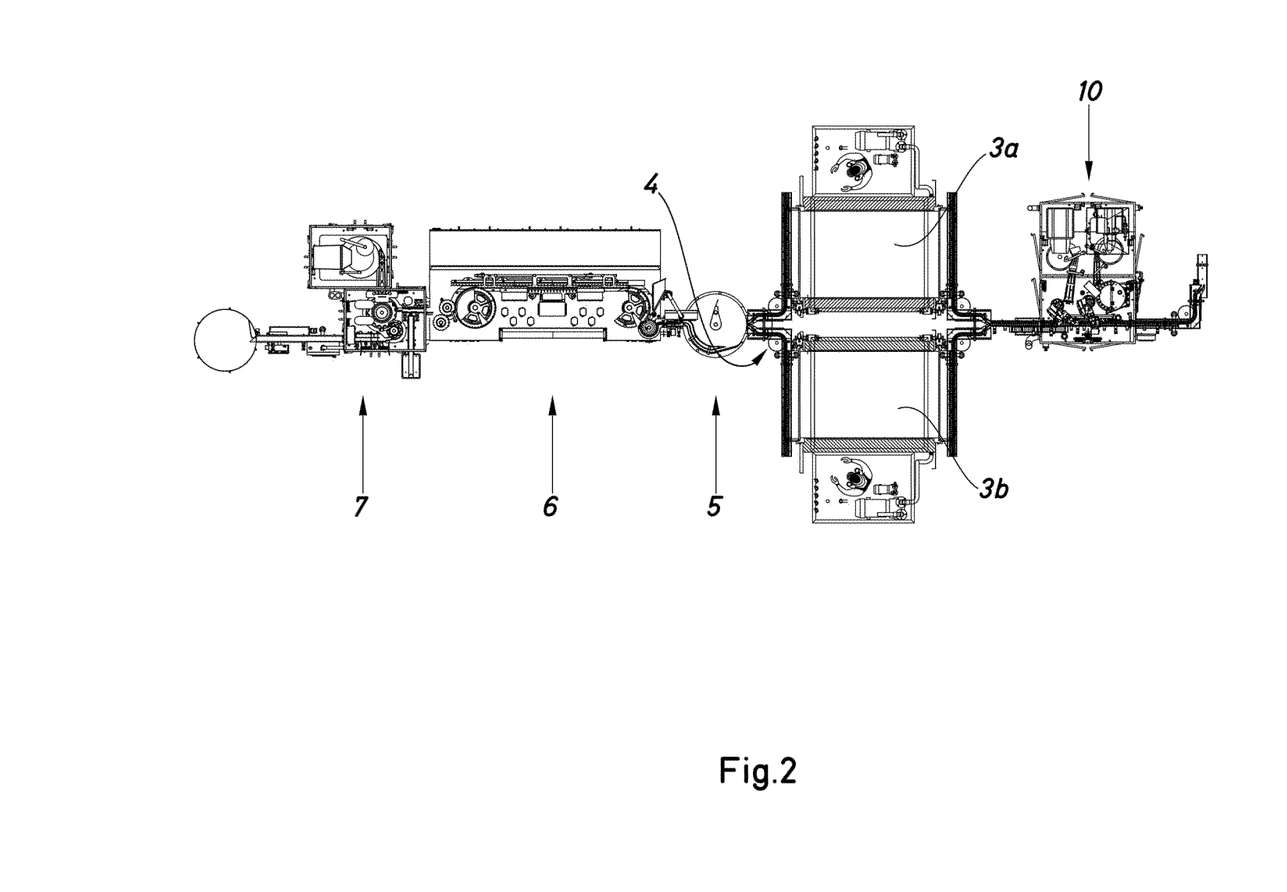
FIG. 2 is a diagram of a second embodiment of a system for the sterile filling of containers for pharmaceutical products, with two parallel autoclaves.
Figure 3:
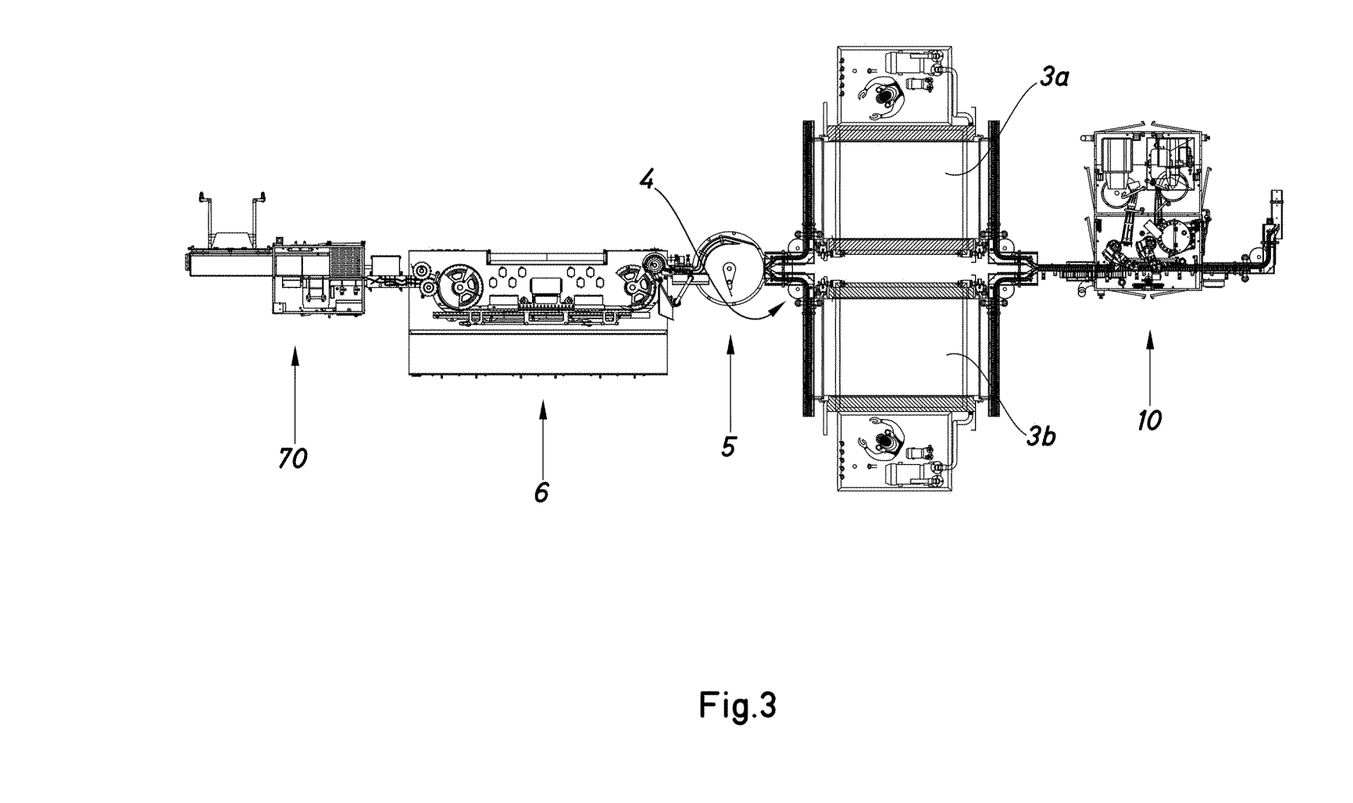
FIG. 3 is a diagram of a third embodiment of a system for the sterile filling of containers for pharmaceutical products, with two parallel autoclaves.

FIGS. 1, 2 and 3 disclose a system for the sterile filling of containers for pharmaceutical products.

The system of FIGS. 1 and 2 shows a first and a second embodiment of systems for the sterile filling of containers, wherein the containers are filled with a liquid pharmaceutical substance, product or drug. In the examples shown, the containers are vials. The system of FIG. 3 shows a system for the sterile filling of containers, wherein the containers are filled with liquid substances, products or drugs which are to be lyophilised subsequently. The lyophilisation process may be of any known type and is not detailed in this patent. In the figures, the same or similar reference numerals refer to analogous elements in each embodiment.

The system for the sterile filling of containers of FIG. 1 comprises a device for sterilising containers, which is a first autoclave 3a, and a machine 6 for filling sterilised containers. In addition, the system comprises a second autoclave 3b arranged or installed parallel to the first autoclave 3a. The system may also comprise at least one additional autoclave connected parallel to the first and second autoclaves (not shown in the figures).

In the system of FIGS. 1 and 2, the containers are transported by automatic transport means, which may be a conveyor belt or another transport device, through a cleaning station positioned in at least one cleaning device prior to sterilisation in the autoclaves 3a, 3b. In this container-cleaning station, the containers are cleaned and dried so as to remove any substance or particle that may be found thereon. The cleaning station may comprise several cleaning and/or drying devices 1, as shown in FIG. 1, or may comprise a single cleaning and drying device 10, as shown in FIG. 2. Depending on the size of the vials, it is advisable to have a station with several cleaning and drying devices. Normally, when the substances to be placed in the vials are liquid substances, the vials used are larger than for powdery substances, and therefore the presence of several cleaning devices is recommended.

The automatic transport means carry the containers to the autoclaves 3a, 3b. These automatic transport means are configured to direct the vials to a second autoclave 3b when a first autoclave 3a is in operation. In addition, the system may comprise an accumulator. This accumulator facilitates the automatic feeding of the vials into the autoclaves 3a, 3b. Preferably, the accumulator comprises an automatic container-diverting device and control means configured to facilitate the vials being directed to a second autoclave 3b when a first autoclave 3a is in operation.

Automating the process of feeding the vials into the autoclaves makes it possible to do away with the idle times that occur when the autoclaves are being loaded/unloaded manually. Thus, once the vials are loaded in the first autoclave 3 a, the sterilisation thereof begins. While the first autoclave 3 a is in operation, the accumulator 8 fills the second autoclave 3 b, allowing the second autoclave 3 b to be in operation whilst the first autoclave 3 a is being unloaded. Since there are two autoclaves in parallel, the vial sterilisation process is faster, and there are no idle times during which none of the autoclaves is operating. This alternating of autoclaves may be carried out at regular intervals.

This automation also does away with the need for operators to have to constantly load/unload the vials in the autoclaves. This minimises the risk of contaminating containers inside the autoclave with microbes and particles from the protective clothing.

The system may have more additional autoclaves positioned parallel to the first and second autoclaves 3a, 3b. The presence of additional autoclaves allows the process to be even more streamlined.

Once the vials have been sterilised in the autoclaves, an automated autoclave-emptying device 4 directs the vials from both autoclaves to a container-accumulation device, which is an accumulation plate 5. This accumulation plate 5 receives the sterilised vials from both autoclaves and directs said vials to the container-filling machine 6 by automatic transport means. Said automatic transport means may be a conveyor belt or another transport device.

The combination of the automatic transport means and the accumulation device allows a constant flow of containers from the plate to the container-filling machine 6, optimising the efficiency of said filling machine 6.

The filling machine 6 may be a metered-feeding device of a known type, which fills the vials aseptically. In the example of FIGS. 1 and 2, following the filling step the vials are duly capped in a capping device 7. In the example of FIG. 3, the vials are placed on trays in a tray-placement device 70, said vials then being capped outside the system described in this patent. The capping of the vials may be carried out as an aseptic process using sterilised caps, or as a clean process outside the aseptic zone. To ensure the required conditions and minimise direct human intervention in the capping process, restricted access barriers and isolators may be beneficial.

FIG. 2 shows a container-filling system similar to that of FIG. 1, with only one container-cleaning device 10.

FIG. 3 shows a container-filling system similar to that of FIGS. 2 and 3, with a tray-placement device 70. Said tray-placement device 70 is used as a transition stage before the lyophilisation process and after capping vials of powdery substances, such as those that are lyophilised, for example. In this case capping is carried out in several steps, this capping being of a known type and not an object of this patent. Normally, the vials to be lyophilised subsequently are smaller than the vials that do not need to be lyophilised, and therefore the system of FIG. 3 comprises a single container-cleaning device 10.

Figure 4:
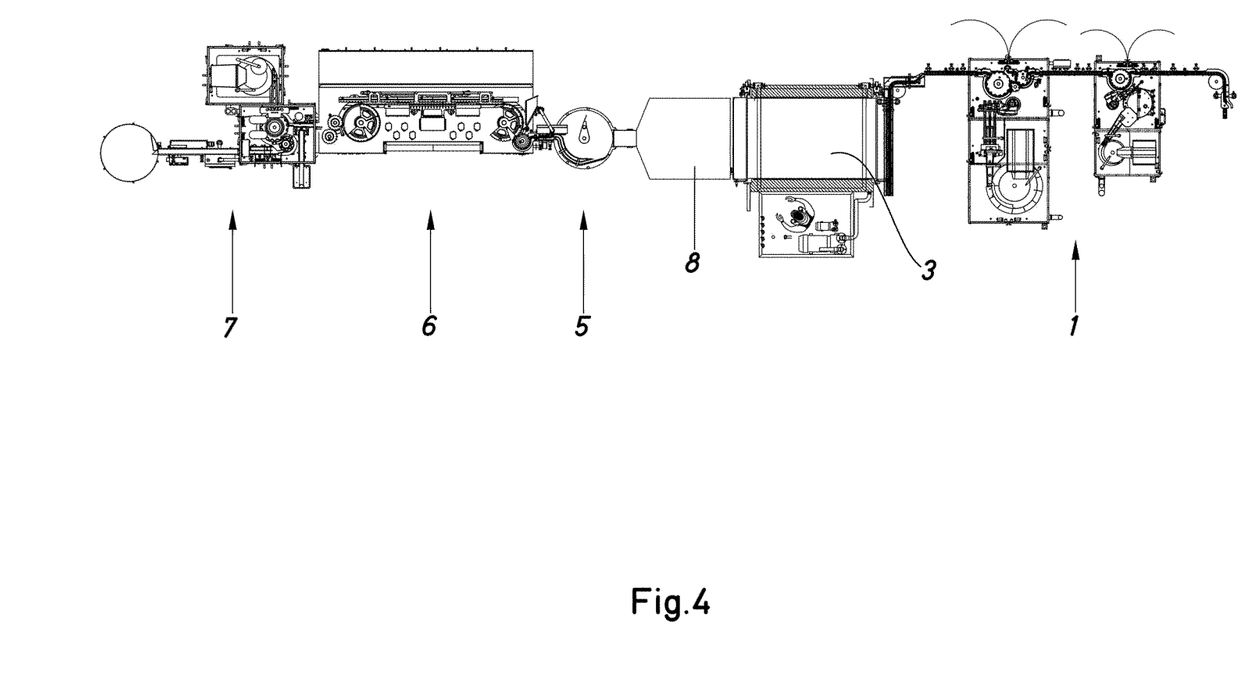
FIG. 4 is a diagram of a fourth embodiment of a system for the sterile filling of containers for pharmaceutical products, with a buffer at the output of the autoclave.
Figure 5:
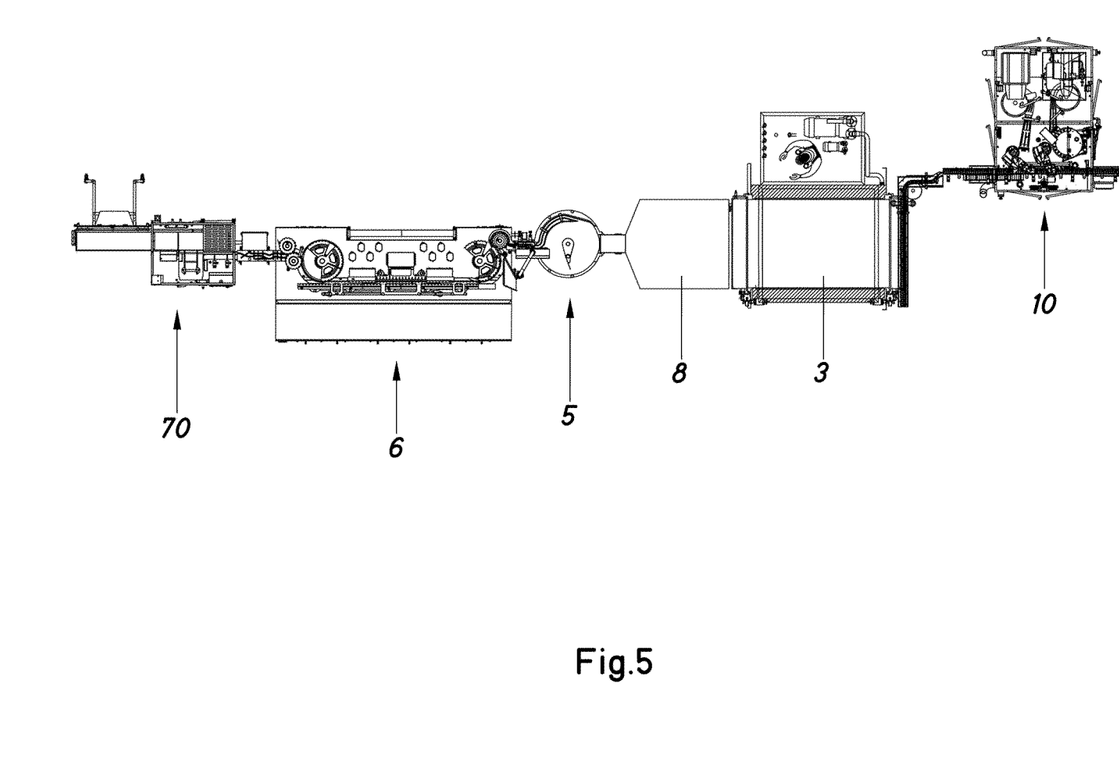
FIG. 5 is a diagram of a fifth embodiment of a system for the sterile filling of containers for pharmaceutical products, with a buffer at the output of the autoclave.

FIGS. 4 and 5 show a system for the sterile filling of containers for pharmaceutical products, which comprises a single autoclave 3, and wherein the accumulation device comprises an intermediate store or buffer 8. As shown in FIGS. 4 and 5, the accumulation device comprises a buffer 8 in addition to an accumulation plate 5. In these figures, elements analogous to those shown in FIGS. 1, 2 and 3 are shown with the same or similar reference numerals.

As in the previous figures, the containers are transported by automatic transport means, which may be a conveyor belt or another transport device, through a cleaning station positioned in at least one cleaning device prior to sterilisation in the autoclave 3. The cleaning station may comprise several cleaning and/or drying devices 1, as shown in FIG. 4, or may comprise a single cleaning and drying device 10, as shown in FIG. 5. The automatic transport means carry the containers to the autoclave 3.

Once the vials have been sterilised in the autoclave 3, the containers pass through an accumulator or buffer 8 and an accumulation plate 5 before being directed to the container-filling machine 6. The accumulator 8 unloads the entire group or batch of sterilised containers and directs said containers in a more continuous flow to an accumulation plate 5. This accumulation plate 5 receives the vials from both autoclaves and directs said vials to the container-filling machine 6 by means of a conveyor belt or another transport device.

The accumulator or buffer 8 is positioned at the output of the autoclave 3, and allows the containers to be unloaded automatically from the autoclave with no human interaction. The combination of the buffer 8 and the accumulation plate 5 allows the sterilised containers to be fed constantly into the filling machine 6. This emptying also allows for faster unloading of containers from the autoclave, and therefore allows the autoclave to be loaded again more quickly with a new batch, streamlining the sterile filling of containers.

Unlike the system of FIGS. 1, 2 and 3, the system does not comprise an accumulator at the input to the autoclave or a diverting device at the output thereof.

FIG. 4 shows a container-filling system with several cleaning and/or drying devices 1 and a capping device 7, while FIG. 5 shows a configuration of a container-filling system with a single cleaning and drying device 10 and with a tray-placement device 70 positioned at the output of the filling machine 6. Other configurations that have not been shown may be possible.

Figure 6:
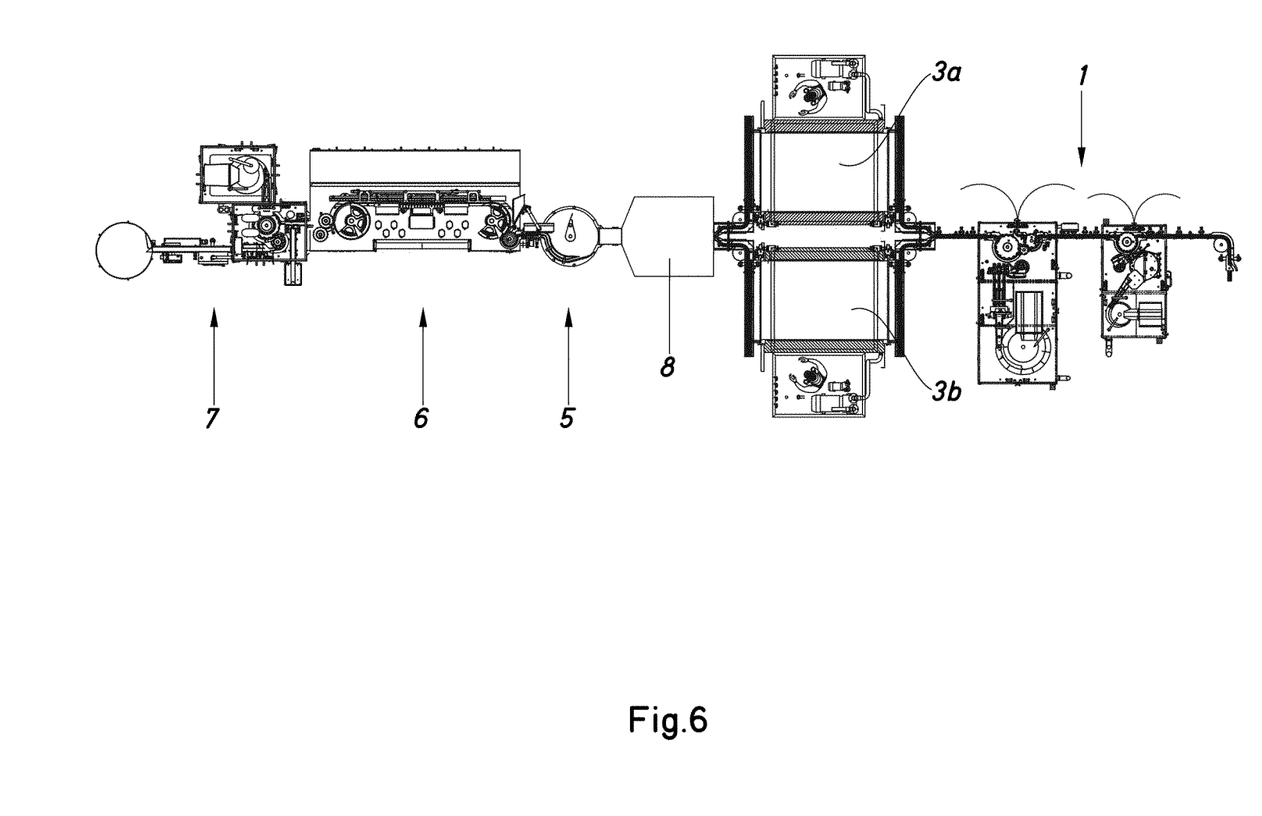
FIG. 6 is a diagram of a sixth embodiment of a system for the sterile filling of containers for pharmaceutical products, with two parallel autoclaves and a single buffer.
Figure 7:
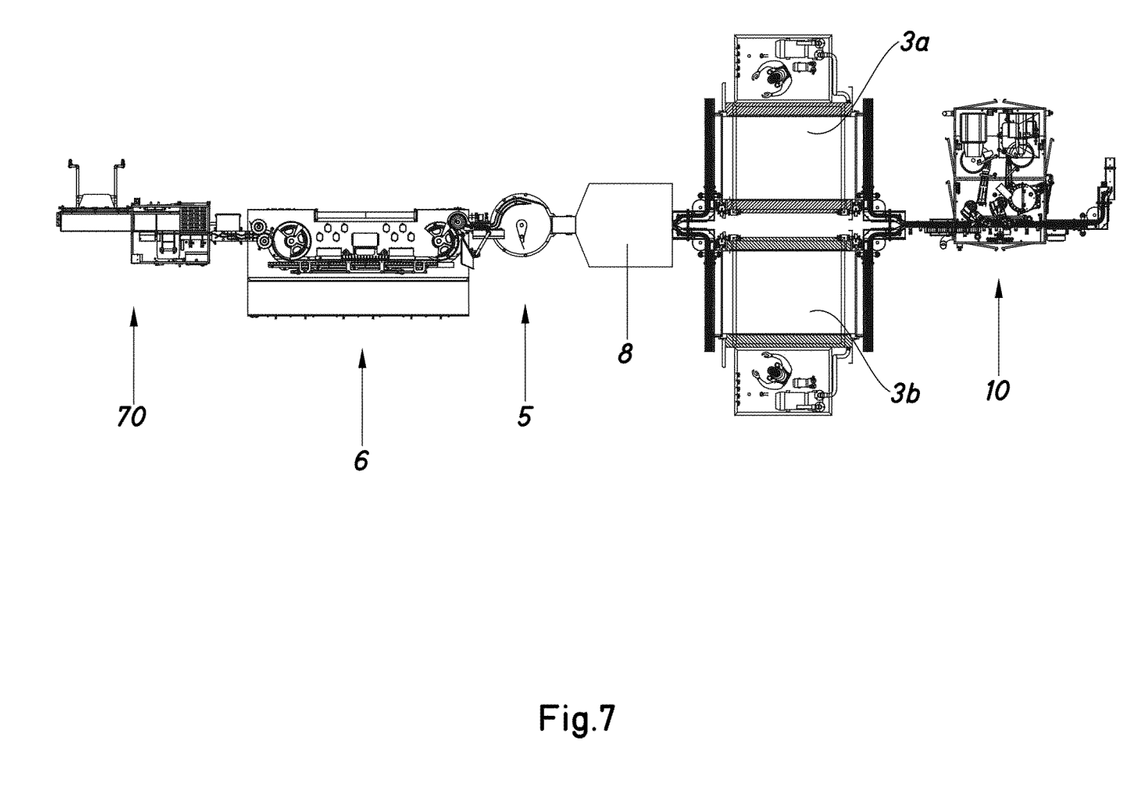
FIG. 7 is a diagram of a seventh embodiment of a system for the sterile filling of containers for pharmaceutical products, with two parallel autoclaves and a single buffer.

FIGS. 6 and 7 show a system for the sterile filling of containers for pharmaceutical products, which comprises two autoclaves 3a and 3b, the second autoclave 3b being positioned parallel to the first autoclave 3a. The system also comprises an accumulation device which comprises a buffer 8 and an accumulation plate 5. In these figures, elements analogous to those shown in the previous figures are shown with the same or similar reference numerals.

As in the previous figures, the containers are transported by automatic transport means, which may be a conveyor belt or another transport device, through a cleaning station positioned in at least one cleaning device prior to sterilisation in the autoclave 3. The cleaning station may comprise several cleaning and/or drying devices 1, as shown in FIG. 6, or may comprise a single cleaning and drying device 10, as shown in FIG. 7. The automatic transport means carry the containers to the autoclaves 3a, 3b, preferably via an input accumulator which facilitates the automatic feeding of the vials into the autoclaves 3a, 3b and which comprises an automatic container-diverting device and control means configured to facilitate the vials being directed to a second autoclave 3b when a first autoclave 3a is in operation. The system may have more additional autoclaves positioned parallel to the first and second autoclave 3a, 3b.

After sterilisation in one of the autoclaves, the containers are unloaded from the autoclaves, preferably by means of an automated autoclave-emptying device, to a container-accumulation device which comprises a buffer 8 and an accumulation plate 5. Alternatively, the buffer 8 is positioned between the emptying device of the first and second autoclaves and the accumulation plate (see FIGS. 6 and 7). In this case, the combination of the buffer 8, which has greater capacity than that of the accumulation plate 5, with said plate 5, allows for a more fluid flow of containers from the autoclaves to the filling machine 6 than that shown in FIGS. 1, 2 and 3. As in the previous embodiments, the accumulation plate 5 directs the sterilised vials to the container-filling machine 6 by automatic transport means. These automatic transport means may be a conveyor belt or another transport device.

FIG. 6 shows a container-filling system with several cleaning and/or drying devices 1 and a capping device 7, while FIG. 7 shows a configuration of a container-filling system with a single cleaning and drying device 10 and with a tray-placement device 70 positioned at the output of the filling machine 6. Other configurations that have not been shown may be possible.

Figure 8:
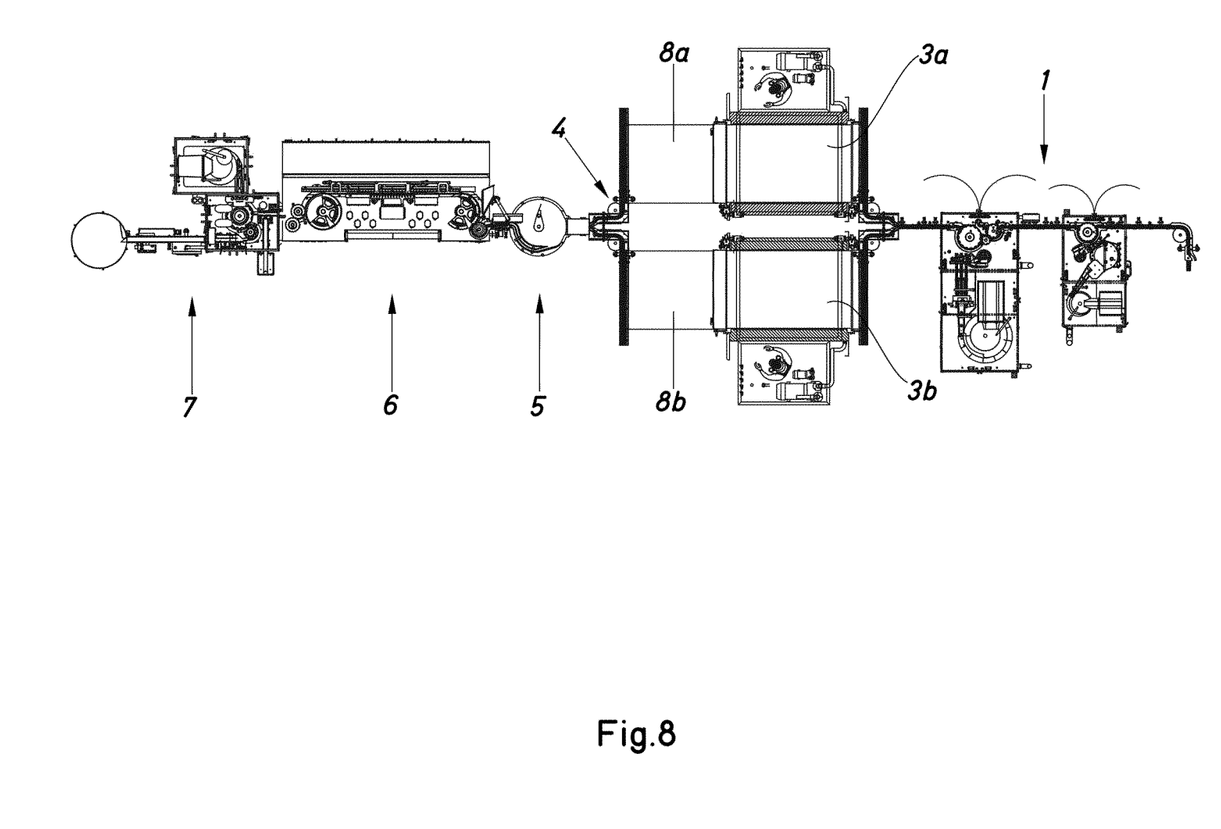
FIG. 8 is a diagram of an eighth embodiment of a system for the sterile filling of containers for pharmaceutical products, with two parallel autoclaves and a buffer at the output of each autoclave.
Figure 9:
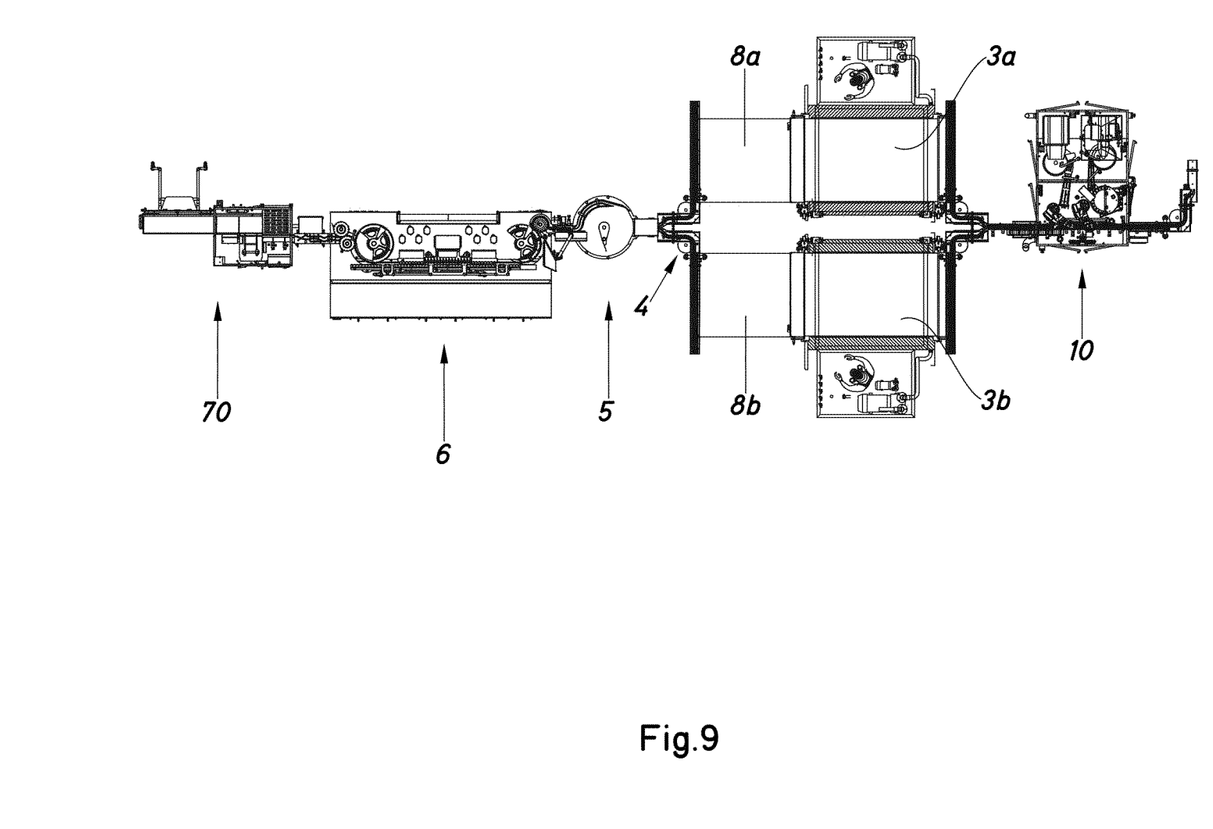
FIG. 9 is a diagram of a ninth embodiment of a system for the sterile filling of containers for pharmaceutical products, with two parallel autoclaves and a buffer at the output of each autoclave.

FIGS. 8 and 9 show a system for the sterile filling of containers for pharmaceutical products, which comprises two autoclaves 3a and 3b, similar to the systems of FIGS. 6 and 7. In this case, the accumulation device comprises a buffer 8a, 8b positioned at the output of each of the autoclaves 3a, 3b. In this case, the automated autoclave-emptying device unloads the containers from the buffers 8a, 8b and directs said containers to an accumulation plate 5.

One of the advantages of having a buffer 8a, 8b in each autoclave is that it allows autoclaves to be emptied with a smaller number of containers per batch, which also allows one of the sets of autoclave and buffer to operate if a second one is undergoing maintenance.

In these figures, elements analogous to those shown in the previous figures are shown with the same or similar reference numerals.

The present invention also discloses a method for the sterile filling of containers for pharmaceutical products. The method according to the present invention is carried out using any of the systems described above and shown in the embodiments of the figures.

The method comprises a step of cleaning containers in a container-cleaning station (which may be carried out in one step using a single device 10 or in two steps using a system with two devices 1); the transport of said containers via automatic transport means to at least one autoclave 3, preferably to at least two autoclaves 3a, 3b positioned parallel to one another; a step of sterilising containers in the autoclaves 3, 3a, 3b; an accumulation step in an accumulation device, said accumulation device comprising an accumulation plate 5, and preferably at least one buffer 8, 8a, 8b; a preferred step of emptying the autoclaves by means of an automated autoclave-emptying device 4, which directs the containers to an accumulation plate 5; the transport of the containers via automatic transport means from the accumulation plate 5 to a container-filling machine 6 which is a metered-feeding device and which fills the vials aseptically; a step of filling containers in said container-filling machine 6; and a step of capping the containers. The filling step is carried out in a similar way both when the injected substance, product or drug is a liquid which is to be lyophilised subsequently and when said substance, product or drug does not need to be lyophilised.

The transport of the containers using a conveyor belt from the filling step to the at least one autoclave may be carried out via an accumulation device. If there is more than one autoclave, the accumulation device may also comprise an automatic diverting device with control means configured to direct the containers to one of the two autoclaves 3a, 3b positioned parallel to one another.

The sterilisation step may be carried out in any number of autoclaves positioned in parallel. The use of an additional autoclave to the autoclaves 3a, 3b mentioned above brings an additional improvement to the overall container-sterilisation time.

The problem with the autoclave 3 is that the container input/output in same is carried out in batches, or lots, and the filling machine 6 cannot absorb peak workloads. Automation of the process allows containers to arrive at the filling machine 6 constantly.

Moreover, quality control may be carried out during the container-sterilisation step. In this quality control, the operators visually or automatically inspect the sterilisation process in the autoclaves and the quality of the containers already sterilised.

Although the invention has been described and shown based on several representative examples, it will be understood that said embodiments are an example and in no way limit the present invention, and therefore any variations that are included directly or by equivalence in the content of the accompanying claims shall be deemed to fall within the scope of the present invention.

What is claimed is:

1. A system for the sterile filling of containers for pharmaceutical products, comprising:
   a device for sterilizing containers; and
   a sterilized-containers filling machine,
   wherein the device for sterilizing containers comprises at least a first autoclave, and wherein the system comprises an automated container-accumulation device and means for automatically transporting the containers sterilized in the autoclave from said autoclave to the sterilized-containers filling machine via said container-accumulation device;
   wherein the container-accumulation device comprises an accumulating plate, wherein the sterilized-containers are directed to the accumulation plate via the means for automatically transporting the containers, and wherein the accumulation plate is configured to direct the at least some of the sterilized containers to the sterilized-containers filling machine via the means for automatically transporting the containers.

2. The system according to claim 1, wherein the container-accumulation device comprises a buffer.

3. The system according to claim 1, wherein the device for sterilizing containers comprises a second autoclave, said second autoclave is being positioned parallel to said first autoclave.

4. The system according to claim 3, wherein the device for sterilizing containers further comprises said second autoclave and a third autoclave parallel to the first autoclave.

5. The system according to claim 3, wherein the device for sterilizing containers comprises an automated autoclave-emptying device, said autoclave-emptying device and the container-filling machine being connected via the container-accumulation device.

6. The system according to claim 3, further comprising an accumulator for filling the autoclaves, the accumulator comprising an automatic container-diverting device and control means configured to direct the containers to the second autoclave when the first autoclave is in operation.

7. The system according to claim 1 further comprising a buffer at an output of each autoclave.

8. The system according to claim 1 further comprising a container-cleaning device and means for automatically transporting the cleaned containers to the at least one autoclave.

9. The system according to claim 1 further comprising a device for capping containers after the container-filling machine.

10. The system according to claim 1, wherein the containers are vials.

11. A method for the sterile filling of containers for pharmaceutical products, comprising steps of:
   cleaning the containers;
   automatically directing a group of the clean containers to an autoclave;
   sterilizing the group of clean containers in the autoclave;
   directing the sterilized containers to a clean zone, via an accumulation plate in an accumulation device; and
   filling the sterilized containers in the clean zone.

12. The method according to claim 11, wherein the accumulation device further comprises a buffer.

13. The method according to claim 11, further comprising arranging a second autoclave parallel to a first autoclave so that, while the clean containers are being sterilized in the first autoclave, the second autoclave is being loaded with new clean containers.

14. The method according to claim 11, further comprising capping of the filled containers.

15. The method according to claim 11, wherein the containers are vials.

* * * * *